United States Patent [19]

Anthony

[11] 4,264,680
[45] Apr. 28, 1981

[54] UV-STABILIZED POLYCARBONATES

[75] Inventor: Blair T. Anthony, Schenectady, N.Y.

[73] Assignee: General Electric Company, Schenectady, N.Y.

[21] Appl. No.: 157,392

[22] Filed: Jun. 9, 1980

[51] Int. Cl.$^3$ .................. B32B 27/36; C07C 121/75; C08K 5/10
[52] U.S. Cl. ........................ 428/412; 260/45.85 A; 260/465 D
[58] Field of Search .................. 260/465 D, 45.85 A; 428/412

[56] References Cited

U.S. PATENT DOCUMENTS

| | | | |
|---|---|---|---|
| 3,215,725 | 11/1965 | Strobel et al. | 260/465 D |
| 4,135,007 | 1/1979 | Lorenz et al. | 428/412 X |
| 4,207,253 | 6/1980 | Lorenz et al. | 260/465 D |

*Primary Examiner*—Dolph H. Torrence
*Attorney, Agent, or Firm*—Joseph T. Cohen; James C. Davis, Jr.

[57] ABSTRACT

Polycarbonate resins can be stabilized against the adverse influence of UV light by incorporating either directly into the resin or by means of a coating on the surface of the polycarbonate resin, an effective amount of a dicyano stabilizer.

7 Claims, No Drawings

UV-STABILIZED POLYCARBONATES

This invention is concerned with stabilized polycarbonate compositions comprising an admixture either directly incorporated into the polymer or as a coating on the surface of said polycarbonate resin, an effective amount of a dicyano stabilizer (hereinafter so designated) of the formula

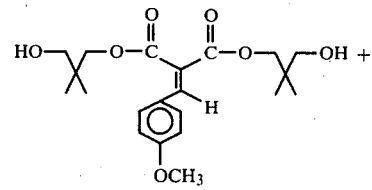

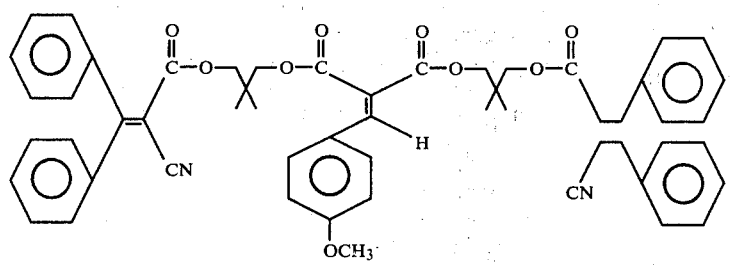

Polycarbonate polymers are excellent molding materials since products made therefrom have high impact strength, toughness, high transparency, wide temperature limits, and good dimensional stability. In particular, polycarbonate resins in the form of film or sheet materials in varying thicknesses, for instance, as protective film or for glazing purposes, have been extensively used because of the foregoing properties inherent in the polycarbonate resin. However, such polycarbonate resins are deficient in their ability to resist the effects of UV light which causes the polycarbonate resin to become colored and yellow under the continuing influence of UV light. Various UV stabilizers have been used in combination with polycarbonate resins to reduce the effect of coloring induced by UV light with varying success. One of the problems of using the usual UV stabilizer is that in molding the polycarbonate resin at elevated temperatures with the UV stabilizer therein, because of the higher volatility of usual stabilizers, losses of the stabilizer occur during the molding or film forming cycle, thereby reducing the stabilizer content with concomitant reduction in resistance to UV light. Moreover, even some of the more prominent UV stabilizers when incorporated in polycarbonate resins are unable to prevent yellowing of the polycarbonate resin being subjected to UV light for extended periods of time.

Unexpectedly, I have discovered that a dicyano stabilizer of formula I can be incorporated in a polycarbonate resin in relatively small amounts or can be applied to the surface of any film or sheet materials made from such polycarbonate resin, either by itself or dispersed in the form of either a coating derived from the polycarbonate resin or a coating derived from another resin, such as polymethacrylate resin (which coatings can be applied in relatively thin coatings with the dicyano stabilizer therein) to give marked improvements in resistance to the UV light and in reduction in the loss of the stabilizer at elevated temperatures.

The UV stabilizer of formula I employed in the practice of the present invention can be prepared in accordance with the equation as shown below.

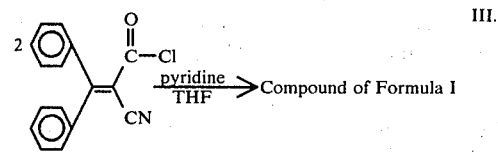

In preparing the dicyano stabilizer of formula I, the dihydroxy compound of formula II can be prepared by reacting p-methoxybenzylidenedimethyl malonate having the formula:

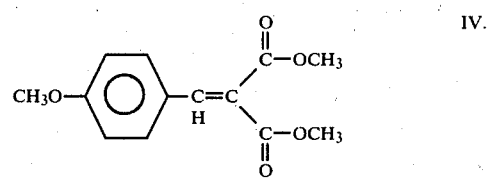

(which is a stabilizer known as Cyasorb 1988 manufactured by American Cyanamide) with neopentyl glycol in the presence of sodium methoxide to give the compound of formula II. The compound of formula IV can be made from p-methoxybenzaldehyde and dimethyl malonate. More particular directions for making the compound of formula II can be found disclosed in the copending application of Ta-Yen Ching, Ser. No. 123,668, filed Feb. 22, 1980 and assigned to the same assignee as the present invention. By reference, this application is made part of the disclosures of the instant application.

The compound of formula III can be prepared by reacting a compound of the formula

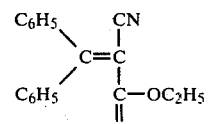

(also known as Uvinul N-35 manufactured by General Aniline)

with NaOH to give the compound of formula

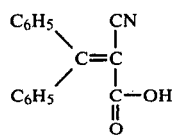

which when reacted with SOCl₂ (thionyl chloride) gives the compound of formula III. Compounds of formula V and methods of preparing the same can be found disclosed in U.S. Pat. No. 3,644,466 issued Feb. 22, 1972 and U.S. Pat. No. 3,180,855 issued Apr. 27, 1965.

The compound of formula II can then be reacted with the compound of formula III as prescribed in the above-identified equation at temperatures ranging from 20° to 50° C., in the presence of pyridine as a hydrohalide acceptor, and tetrahydrofuran as a solvent, to give the desired UV stabilizer of formula I.

The aromatic polycarbonate resins which can be employed in the practice of the present invention are homopolymers and copolymers and mixtures thereof which have an intrinsic viscosity (I.V.) of 0.30 to 1.0 dl./g. or more as measured in methylene chloride at 25° C. and are prepared by reacting a dihydric phenol with a carbonate precursor. Typical of some of the dihydric phenols that may be employed in the practice of this invention are bisphenol-A [2,2-bis(4-hydroxyphenyl)-propane], bis(4-hydroxyphenyl) methane, 2,2-bis(4-hydroxy-3-methylphenyl) propane, 4,4-bis(4-hydroxyphenyl) heptane, 2,2-(3,5,3',5'-tetrachloro-4,4'-dihydroxydiphenyl) propane, 2,2-(3,5,3',5'-tetrabromo-4,4'-dihydroxydiphenyl)-propane, (3,3'-dichloro-4,4'-dihydroxydiphenyl) methane, etc. Other dihydric phenols of the bisphenol type are also available and are disclosed in U.S. Pat. Nos. 2,999,835, 3,028,365 and 3,334,154.

It is, of course, possible to employ two or more different dihydric phenols for making copolymers of a dihydric phenol with a glycol or with a hydroxy or acid terminated polyester, or with a dibasic acid in the event a carbonate copolymer or inter-polymer rather than a homopolymer is desired for use in the preparation of the aromatic carbonate polymers of this invention. Also employed in the practice of this invention may be blends of any of the above materials to provide the aromatic carbonate polymer.

The carbonate precursor may be either a carbonyl halide, a carbonate ester or a haloformate. The carbonyl halides which can be employed herein are carbonyl bromide, carbonyl chloride and mixtures thereof. Typical of the carbonate esters which may be employed herein are diphenyl carbonate, di-(halophenyl) carbonates such as di-(chlorophenyl) carbonate, di-(bromophenyl) carbonate, di-(trichlorophenyl) carbonate, di-(tribromophenyl) carbonate, etc. di-(alkylphenyl) carbonates such as di(tolyl) carbonate, etc., di-(naphthyl) carbonate, di-(chloronaphthyl) carbonate, phenyl tolyl carbonate, chlorophenyl chloronaphthyl carbonate, etc. or mixtures thereof. The haloformates suitable for use herein include bis-haloformates of dihydric phenols (bischloroformates of hydroquinone, etc.) or glycols (bishaloformates of ethylene glycol, neopentyl glycol, polyethylene glycol, etc.). While other carbonate precursors will occur to those skilled in the art, carbonyl chloride, also known as phosgene, is preferred.

Also included are the polymeric derivatives of a dihydric phenol, a dicarboxylic acid and carbonic acid. These are disclosed in U.S. Pat. No. 3,169,121 which is incorporated herein by reference.

The aromatic carbonate polymers of this invention may be prepared by employing a molecular weight regulator, an acid acceptor and a catalyst. The molecular weight regulators which can be employed in carrying out the process of this invention include monohydric phenols such as phenol, chroman-I, paratertiarbutylphenol, parabromophenol, primary and secondary amines, etc. Preferably, phenol is employed as the molecular weight regulator.

A suitable acid acceptor may be either an organic or an inorganic acid acceptor. A suitable organic acid acceptor is a tertiary amine and includes such materials as pyridine, triethylamine, dimethylaniline, tributylamine, etc. The inorganic acid acceptor may be one which can be either a hydroxide, a carbonate, a bicarbonate, or a phosphate of an alkali or alkaline earth metal.

The catalysts which are employed herein can be any of the suitable catalysts that aid the polymerization of bisphenol-A with phosgene. Suitable catalysts include tertiary amines such as, for example, triethylamine, tripropylamine, N,N-dimethylaniline, quaternary ammonium compounds such as, for example, tetraethylammonium bromide, cetyl triethyl ammonium bromide, tetra-n-heptylammonium iodide, tetra-n-propyl ammonium bromide, tetramethylammonium chloride, tetramethyl ammonium hydroxide, tetra-n-butyl ammonium iodide, benzyltrimethyl ammonium chloride and quaternary phosphonium compounds such as, for example, n-butyltriphenyl phosphonium bromide and methyltriphenyl phosphonium bromide.

Also, included herein are branched polycarbonates wherein a polyfunctional aromatic compound is reacted with the dihydric phenol and carbonate precursor to provide a thermoplastic randomly branched polycarbonate.

These polyfunctional aromatic compounds contain at least three functional groups which are carboxyl, carboxylic anhydride, haloformyl or mixtures thereof. Examples of these polyfunctional aromatic compounds which may be employed in the practice of this invention include: trimellitic anhydride, trimellitic acid, trimellityl trichloride, 4-chloroformyl phthalic anhydride, pyromellitic acid, pyromellitic dianhydride, mellitic acid, mellitic anhydride, trimesic acid, benzophenonetetracarboxylic acid, benzophenonetetracarboxylic anhydride and the like. The preferred polyfunctional aromatic compounds are trimellitic anhydride or trimellitic acid or their haloformyl derivatives. Also, included herein are blends of a linear polycarbonate and a branched polycarbonate.

In order that those skilled in the art might better understand how the present invention may be practiced, the following examples are given by way of illustration and not by way of limitation. All parts are by weight unless otherwise indicated.

EXAMPLE 1

This example illustrates the preparation of the UV stabilizer of formula I. More particularly, to a 30 ml pyridine solution of 2.0 grams (0.005 mole) of compound II was added dropwise at room temperature (about 25°–30° C.) a solution of 2.7 grams (0.01 mole) of compound III dissolved in 40 ml tetrahydrofuran. The mixture was then allowed to react at ambient temperature for about 18 hours with continued stirring. The reaction mixture was then washed with a 5% aqueous solution of HCl, 5% aqueous solution of sodium bicarbonate, and thereafter with water. The organic layer which separated was dried over magnesium sulfate, filtered, and the solvent removed to produce white crystals which when recrystallized from methanol yielded the pure dicyano compound of formula I, having a melting point of 77°–80° C. The identity of this compound was established by NMR analyses and by elemental analyses: Calculated—C 74.3%, H 5.6%, N 3.3%, O 16.8%; Found—C 74.19%, H 5.74%, N 3.15%, O 16.77%.

EXAMPLE 2

Employing the compound of formula I, a 21.5 weight percent solids solution employing a polymethylmethacrylate resin dissolved in butyl cellosolve was prepared. This polymethyl methacrylate resin containing 5%, by weight, of the dicyano compound, based on the weight of the methacrylate resin, was flow-coated onto a polycarbonate resin sheet and allowed to drain vertically for 30 minutes at room temperature. After the polycarbonate resin sheet was heated in a vented oven for one hour at 125° to cure the resin and remove the solvent, the thickness of the cured methacrylate coating on the polycarbonate resin substrate was about 0.30 mil.

EXAMPLE 3

In this example, a determination was made as to the ability of the UV stabilizer of formula I to remain in the polycarbonate-polymethylmethacrylate system after heat-aging the coated polycarbonate resin of Example 2 at 125° C. as shown in Table II. For comparison, three other well known UV stabilizers were applied to a polycarbonate substrate in the same manner as was done with the dicyano stabilizer of formula I. The three stabilizers used were commercially available and are found described in Table I where the formulas for each commercial UV stabilizer are shown. The rate of photoaging was also evaluated under a reflector sunlamp (RS) kept 8 inches above the sample which was spun slowly (about 10 revolutions per minute) on a turntable in a vented hood at 30° C. The yellowing index (YI) of the samples was periodically measured on an XL-20 Digital Tristimulus Calorimeter. The rate of photoaging of the samples containing the UV stabilizer of formula I was greatly reduced as compared to the other commercial stabilizers (Uvinul N-35 and Uvinul N-539 both manufactured by General Aniline Company, and Cyasorb 1988 manufactured by American Cyanamide Company) as shown in the following Table I.

TABLE I

| UV Screens | YI | ΔYI After RS Sunlamp Exposure | | | | | |
|---|---|---|---|---|---|---|---|
| | | 168 hrs | 336 hrs | 504 hrs | 672 hrs | 840 hrs | 1008 hrs |
| 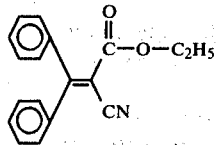 Uvinul N-35 | 1.1 | 2.1 | 3.4 | 4.0 | 5.6 | 6.2 | 6.9 |
| 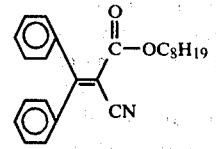 Uvinul N-539 | 1.0 | 0.9 | 1.3 | 2.7 | 4.3 | 6.2 | 6.9 |
| 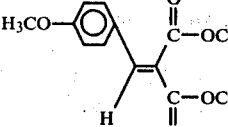 Cyasorb 1988 | 1.1 | 0.7 | 1.5 | 3.4 | 5.1 | 6.1 | 7.3 |
| Compound I | 1.0 | 0.1 | 0.3 | 0.5 | 0.5 | 0.9 | 1.4 |

TABLE II

| | % Screener Remaining After Heat Aging at 125° C. | | | | | |
|---|---|---|---|---|---|---|
| UV Screen (5% by weight in acrylic 2042) | 0 | 1 Hr. | 2 Hrs. | 4 Hrs. | 8 Hrs. | 24 Hrs. |
| Uvinul N-35 | 100% | 58% | 58% | 55% | 55% | 53% |
| Uvinul N-539 | 100% | 84% | 75% | 68% | 54% | 45% |
| Cyasorb 1988 | 100% | 75% | 73% | 68% | 60% | 50% |
| III | 100% | 100% | 99% | 100% | 100% | 100% |

It can be seen from the data in the aforesaid Table I that when the dicyano stabilizer is used in combination with the aromatic polycarbonate resin, the resulting polycarbonate composition has considerably better resistance to UV light, as evidenced by its resistance to yellowing, even after many hundreds of hours of being subjected to a UV source.

It will of course be apparent to those skilled in the art that in addition to the proportions of UV stabilizer incorporated, other proportions may be used with satisfactory results. Thus I can use from 0.5 to 10%, by weight, of the compound of formula I, based on the weight of the resin being stabilized.

The UV stabilizer of formula I can be milled into the polycarbonate resin so that it is intimately dispersed throughout the latter to provide its stabilizing effect. Alternatively, instead of using the polymethacrylate resin for dispersing the UV stabilizer and applying it as a thin coating on the surface of the polycarbonate resin, other resins may be used as dispersing media for the UV stabilizer, such as the polycarbonate resin itself and then applied as a thin coating over the substrate polycarbonate, which can range from 0.1 to 50 mils or more in thickness, especially when used for glazing purposes. Because of the high temperature stability of the UV stabilizer and its very low volatility, the polycarbonate substrate and the resinous medium in which the UV stabilizer is dispersed for positioning on the surface of the polycarbonate substrate, can advantageously be co-extruded at elevated temperatures using equipment readily available for the purpose, to effect a close bond between the upper layer containing the UV stabilizer and the substrate polycarbonate resin.

In addition to providing UV stability for polycarbonate resins, the UV stabilizer of formula I can also be used to stabilize other resinous compositions against the coloring influence of UV light. Among such polymeric compositions which can be so protected are polyester resins, for example, polyethylene terephthalate, polybutylene, terphthalate, etc.; polyimide resins, polyurethane resins, polyphenylene oxide resins as are more particularly disclosed and claimed in U.S. Pat. No. 3,306,875, issued Feb. 28, 1967, etc. It will be found that resins protected by the UV stabilizer employed in the practice of the present invention have far superior outdoor service life than resins using many of the usual UV stabilizers.

It will of course be apparent to those skilled in the art that in addition to the use of the specific dicyano stabilizer of formula I, it is also possible to make dicyano stabilizers of a more generic nature of which the compound of formula I is a species. Thus, other compounds in the class of formula I can be used if the residue from the neopentyl glycol is replaced by X where, in addition to X being the neopentyl group, X can also be a divalent saturated alkylene group, for instance

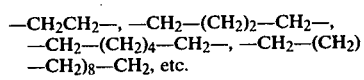
—CH$_2$CH$_2$—, —CH$_2$—(CH$_2$)$_2$—CH$_2$—,
—CH$_2$—(CH$_2$)$_4$—CH$_2$—, —CH$_2$—(CH$_2$)
—CH$_2$)$_8$—CH$_2$, etc.

The generic dicyano stabilizer compounds based on formula I can be prepared similarly as was done for the neopentyl derivative of formula I by substituting in the appropriate place, instead of the neopentyl glycol, a glycol such as ethylene glycol, 1,4-butanediol, 1,6-hexanediol, etc. All other methods for preparing compounds of the generic dicyano stabilizer will follow those used for making the noepentyl dicyano stabilizer of formula I. These other dicyano stabilizers can also be employed for stabilizing various thermoplastic resins, and particularly polycarbonate resins in the same manner as was done using the dicyano stabilizer of formula I.

What I claim as new and desire to obtain by Letters Patent of the United States is:

1. A composition of matter comprising (1) a thermaplastic resin susceptible to degradation by ultraviolet light and (2) an effective amount of a UV stabilizer of the formula

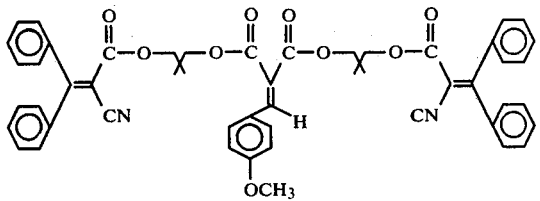

2. A composition of matter comprising (1) a polycarbonate resin susceptible to degradation by ultraviolet light and (2) an effective amount of a UV stabilizer comprising a compound having the formula

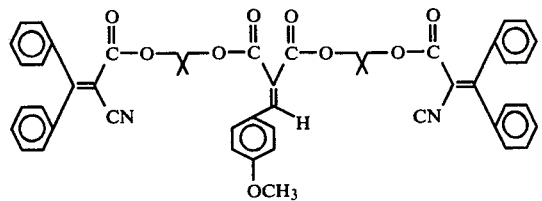

3. A composition as in claim 2 wherein the UV stabilizer is present in an amount ranging from 0.5 to 10%, by weight, based on the weight of the polycarbonate resin.

4. A composition as in claim 2 wherein the polycarbonate resin is in the form of a film or thick sheet.

5. A composition as in claim 2 wherein the UV stabilizer is homogeneously dispersed throughout the polycarbonate resin.

6. A composition as in claim 2 wherein the polycarbonate resin being protected against the effects of ultraviolet light is so protected by means of a thin coating of a resinous composition containing the UV stabilizer dispersed homogeneously throughout the thin coating, which in turn is disposed on the surface of the polycarbonate substrate.

7. A compound of the formula

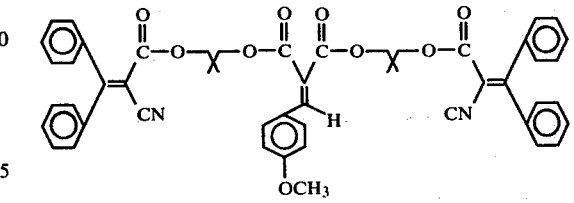

* * * * *